United States Patent
Abudawoud et al.

(10) Patent No.: US 10,005,703 B2
(45) Date of Patent: Jun. 26, 2018

(54) PROPYLENE PRODUCTION USING A MESOPOROUS SILICA FOAM METATHESIS CATALYST

(71) Applicants: Saudi Arabian Oil Company, Dhahran (SA); King Fahd University of Petroleum & Minerals, Dhahran (SA)

(72) Inventors: Raed Abudawoud, Kohbar (SA); Sulaiman Saleh Al-Khattaf, Dhahran (SA); Arudra Palani, Dhahran (SA); Abdullah M. Aitani, Al-Khobar (SA); Mohammad Naseem Akhtar, Dhahran (SA); Tazul Islam Bhuiyan, Dhahran (SA); Mohammed A. Al-Yami, Dhahran (SA)

(73) Assignees: Saudi Arabian Oil Company, Dhahran (SA); King Fahd University of Petroleum & Minerals, Dhahran (SA)

( * ) Notice: Subject to any disclaimer, the term of this patent is extended or adjusted under 35 U.S.C. 154(b) by 0 days. days.

(21) Appl. No.: 15/190,950

(22) Filed: Jun. 23, 2016

(65) Prior Publication Data

US 2017/0001925 A1    Jan. 5, 2017

Related U.S. Application Data

(60) Provisional application No. 62/188,129, filed on Jul. 2, 2015.

(51) Int. Cl.

| | |
|---|---|
| *C07C 6/04* | (2006.01) |
| *B01J 23/30* | (2006.01) |
| *B01J 35/10* | (2006.01) |
| *B01J 21/08* | (2006.01) |
| *B01J 32/00* | (2006.01) |
| *B01J 35/04* | (2006.01) |

(52) U.S. Cl.
CPC ............... *C07C 6/04* (2013.01); *B01J 21/08* (2013.01); *B01J 23/30* (2013.01); *B01J 32/00* (2013.01); *B01J 35/04* (2013.01); *B01J 35/1019* (2013.01); *B01J 35/1023* (2013.01); *B01J 35/1042* (2013.01); *B01J 35/1047* (2013.01); *B01J 35/1061* (2013.01); *B01J 2231/543* (2013.01); *B01J 2523/41* (2013.01); *B01J 2523/68* (2013.01); *B01J 2523/69* (2013.01); *B01J 2523/74* (2013.01); *C07C 2521/08* (2013.01); *C07C 2523/28* (2013.01); *C07C 2523/30* (2013.01); *C07C 2523/36* (2013.01); *C07C 2529/78* (2013.01); *Y02P 20/52* (2015.11)

(58) Field of Classification Search
CPC ....... C07C 6/04; C07C 11/06; C07C 2521/08; C07C 2523/28; C07C 2523/30; C07C 2523/36; C07C 2529/78; B01J 21/08; B01J 2231/543; B01J 23/30; B01J 2523/41; B01J 2523/68; B01J 2523/69; B01J 2523/74; B01J 32/00; B01J 35/04; B01J 35/1019; B01J 35/1023; B01J 35/1042; B01J 35/1047; B01J 35/1061
See application file for complete search history.

(56) References Cited

U.S. PATENT DOCUMENTS

| | | | |
|---|---|---|---|
| 3,586,731 | A | 6/1971 | Heckelsberg |
| 4,024,201 | A | 5/1977 | Takahashi |
| 4,071,471 | A | 1/1978 | Banks |
| 5,026,935 | A | 6/1991 | Leyshon et al. |
| 5,026,936 | A | 6/1991 | Leyshon et al. |
| 6,207,115 | B1 | 3/2001 | Chodorge et al. |
| 6,538,168 | B1 | 3/2003 | Schwab et al. |
| 6,586,649 | B1 | 7/2003 | Botha et al. |
| 6,646,172 | B1 | 11/2003 | Schwab et al. |
| 6,777,582 | B2 | 8/2004 | Gartside et al. |
| 7,214,841 | B2 | 5/2007 | Gartside et al. |
| 7,754,647 | B2 | 7/2010 | Schubert et al. |
| 7,754,934 | B2 | 7/2010 | Tsunoda et al. |
| 8,299,313 | B2 | 10/2012 | Takai et al. |
| 8,324,440 | B2 * | 12/2012 | Popp .................... B01J 21/08 502/232 |
| 8,440,874 | B2 | 5/2013 | Ramachandran et al. |
| 8,586,813 | B2 | 11/2013 | Ramachandran et al. |
| 8,722,568 | B2 | 5/2014 | Popp et al. |
| 2004/0254411 | A1 | 12/2004 | Steinbrenner et al. |
| 2005/0014981 | A1 | 1/2005 | Gartside et al. |

(Continued)

FOREIGN PATENT DOCUMENTS

| | | |
|---|---|---|
| CN | 104370676 A | 2/2015 |
| EP | 304515 B1 | 12/1991 |
| WO | 9929805 A1 | 6/1999 |
| WO | 2006089957 A1 | 8/2006 |
| WO | 2009117128 A1 | 9/2009 |
| WO | 2010019595 A2 | 2/2010 |
| WO | 2011136983 A1 | 11/2011 |
| WO | 2015055594 A1 | 4/2015 |
| WO | 2017-003812 A1 | 1/2017 |

OTHER PUBLICATIONS

International Search Report and Written Opinion dated Sep. 27, 2016 pertaining to International Application No. PCT/US2016/038967.

International Search Report pertaining to PCT/US2016/039025, filed Jun. 23, 2016, 6 pages.

Written Opinion pertaining to PCT/US2016/039025, filed Jun. 23, 2016, 5 pages.

Bin Hu, et al., Highly Active Doped Mesoporous KIT-6 Catalysts for Metathesis of 1-Butene and Ethene to Propene: The Influence of Neighboring Environment of W Species, The Journal of Physical Chemistry, ACS Publication, 2013 American Chemical Society, pp. 26385-26395, USA.

(Continued)

*Primary Examiner* — Sharon Pregler
(74) *Attorney, Agent, or Firm* — Dinsmore & Shohl LLP

(57) ABSTRACT

Embodiments of a metathesis process for producing propylene comprise providing a metathesis catalyst comprising an amorphous mesoporous silica foam impregnated with metal oxides, where the metathesis catalyst has a pore size distribution of at least 3 nm to 40 nm and a total pore volume of at least 0.700 cm³/g. The process further involves producing a product stream comprising propylene by contacting a feed stream comprising butene with the metathesis catalyst.

17 Claims, 2 Drawing Sheets

(56) References Cited

U.S. PATENT DOCUMENTS

| | | |
|---|---|---|
| 2006/0293548 A1 | 12/2006 | Spamer et al. |
| 2007/0038010 A1 | 2/2007 | Xie et al. |
| 2007/0225478 A1 | 9/2007 | Querci et al. |
| 2009/0170692 A1 | 7/2009 | Ying et al. |
| 2011/0021858 A1 | 1/2011 | Ramachandran et al. |
| 2011/0152595 A1 | 6/2011 | Takai et al. |
| 2011/0196185 A1 | 8/2011 | Krawczyk et al. |
| 2012/0108864 A1 | 5/2012 | Gartside et al. |
| 2012/0283090 A1 | 11/2012 | Popp et al. |
| 2012/0289617 A1 | 11/2012 | Wang et al. |

OTHER PUBLICATIONS

Ruihua Gao, et al., High-activity, single-site mesoporous WO3-MCF materials for the catalytic epoxidation of cycloocta-1,5-diene with aqueous hydrogen peroxide, Journal of Catalysis, 256, 2008, pp. 259-267, China.

H. Balcar, et al., Mesoporous molecular sieves as advanced supports for olefin metathesis catalysts, Coordination Chemistry Reviews 257, 2013, pp. 3107-3124, Czech Republic.

Kumar et al., Performance of Nano Crystalline H-ZSM-5 as Additive in FCC Catalyst: A Review, IJRET: International Journal of Research in Engineering and Technology, May 2014, vol. 3, pp. 481-485.

Arudra et al., "Silicalite-1 as Efficient Catalyst for Production of Propene from 1-Butene", ACS Catalysis, 2014, 4205-4212, 4, American Chemical Society.

Awayssa et al., "Modified HZSM-5 as FCC Additive for Enhancing Light Olefins Yield from Catalytic Cracking of VGO", Applied Catalysis A: General, 2014, 172-183, 477.

Barrett et al., "The Determination of Pore Volume and Area Distributions in Porous Substances. I. Computations from Nitrogen Isotherms", J. Am. Chem. Soc., 1951, 373-380, 73(1).

Beck et al., "A New Family of Mesoporous Molecular Sieves Prepared with Liquid Crystal Templates", J. Am. Chem. Soc., 1992, 10834-10843, 114, American Chemical Society.

Bhuiyan et al., "Kinetics Modelling of 2-Butene Metathesis Over Tungsten Oxide Containing Mesoporous Silica Catalyst", The Canadian Journal of Chemical Engineering, 2014, 1271-1282. 92.

Bhuiyan et al., "Metathesis of 2-Butene to Propylene over W-Mesoporous Molecular Sieves: A Comparative Study Between Tungsten Containing MCM-41 and SBA-15", Applied Catalysis A: General, 2013, 224-234, 467, Elsevier B.V.

Do et al., "Zeolite Nanoclusters Coated onto the Mesopore Walls of SBA-15", J. Am. Chem. Soc., 2004, 14324-14325, 126, American Chemical Society.

Jermy et al., "Utilization of ZSM-5/MCM-41 Composite as FCC Catalyst Additive for Enhancing Propylene Yield from VGO Cracking", J. Porous Mater, 2012, 499-509, 19, Springer.

Lwin et al., "Olefin Metathesis by Supported Metal Oxide Catalysts", ACS Catalysis, 2014, 2505-2520, 4, American, Chemical Society.

Wang et al., Synthesis and Structure of Silicalite-1/SBA-15 Composites Prepared by Carbon Templating and Crystallization, Journal of Materials Chemistry, 2007,4265-4273,17, The Royal Society of Chemistry 2007.

Wang et al., "Effect of Support Nature on WO3/SiO2 Structure and Butene-1 Metathesis", Applied Catalysis A: General, 2003, 25-37, 250, Elsevier B.V.

Zhao et al., "Effect of Tungsten Oxide Loading on Metathesis Activity of Ethene and 2-Butene Over WO3/SiO2 Catalysts" Transition Met Chem, 2009, 621-27, 34, Springer.

International Preliminary Report on Patentability dated Jan. 2, 2018 pertaining to International PCT Application No. PCT/US2016/039012.

International Preliminary Report on Patentability dated Jan. 2, 2018 pertaining to International PCT Application No. PCT/US2016/038967.

International Search Report and Written Opinion dated Sep. 14, 2016 pertaining to International Application No. PCT/US2016/039012.

Daniell et al., Enhanced Surface Acidity in Mixed Alumina-Silicas: A Low-Temperature FTIR Study:, 2000, 196, 247-260, Elsevier.

International Search Report and Written Opinion dated Sep. 14, 2016 pertaining to International Application No. PCT/US2016/039013.

International Search Report and Written opinion dated Mar. 28, 2018, pertaining to International Application No. PCT/US2018/013945, filed Jan. 17, 2018, 9 pages.

* cited by examiner

PROPYLENE PRODUCTION USING A MESOPOROUS SILICA FOAM METATHESIS CATALYST

CROSS REFERENCE TO RELATED APPLICATIONS

This application claims priority to U.S. Provisional Application Ser. No. 62/188,129, filed Jul. 2, 2015, the entire contents of which are hereby incorporated by reference.

TECHNICAL FIELD

Embodiments of the present disclosure generally relate to propylene production, and more specifically relate to converting a stream comprising butene to propylene via metathesis using an amorphous mesoporous silica foam metathesis catalyst.

BACKGROUND

In recent years, there has been a dramatic increase in the demand for propylene to feed the growing markets for polypropylene, propylene oxide and acrylic acid. Currently, most of the propylene produced worldwide (74 million tons/year) is a by-product from steam cracking units (57%) which primarily produce ethylene, or a by-product from Fluid Catalytic Cracking (FCC) units (30%) which primarily produce gasoline. These processes cannot respond adequately to a rapid increase in propylene demand. However, the processing of lower cost butenes co-produced by these processes gives the refiner or the petrochemical producer an opportunity to add value depending on downstream integration and relative economics. The so-called on-purpose propylene processes such as propane dehydrogenation (PDH), metathesis of ethylene and butenes, high severity FCC, olefins cracking and methanol to olefins (MTO) contributes about 12% of total propylene production. However, propylene demand growth has exceeded ethylene and gasoline/distillate demand growth, and propylene supply has not kept pace with this increase in demand.

Olefin metathesis is considered a useful reaction to shift the composition of a pool of low-value butenes to meet market demand for propylene. In 2010, propylene production via metathesis accounted for about 5% of global propylene supply. This segment has been the most rapidly growing on-purpose propylene production route over the past 5 years. With new capacity coming on-stream in the Middle East and Asia, propylene production via metathesis is expected to increase.

Catalytic olefin metathesis is a useful chemical reaction that is able to transform simple and cheap organic molecules into complex and valuable molecules. In olefin metathesis, two olefin molecules exchange the groups around the double bonds in the presence of a catalyst. The olefins can be of different molecules by structure and composition, or two identical molecules. In general, reaction temperatures for olefin metathesis reactions can be as low as at room temperature or can be at temperatures up to about 500° C. or greater, depending on the type of starting materials, the catalyst used, and the media in which the reaction is carried out.

However, olefin metathesis catalysts often do not have the requisite selectivity to yield propylene and other products. Additionally, olefin metathesis catalysts are subject to deactivation due to coking from aromatic products.

SUMMARY

Accordingly, ongoing needs exist for catalyst preparation for selective production of propylene using butenes metathesis. Embodiments of the present disclosure are directed to the production of propylene via metathesis using a metathesis catalyst comprising an amorphous mesoporous silica foam impregnated with metal oxides.

According to one embodiment, a metathesis process for producing propylene is provided. The process comprises providing a metathesis catalyst comprising an amorphous mesoporous silica foam impregnated with metal oxides. The metathesis catalyst has a pore size distribution of at least 3 nanometers (nm) to about 40 nm and a total pore volume of at least 0.700 centimers$^3$/gram (cm$^3$/g). The metathesis process further comprises producing a product stream comprising propylene by contacting a feed stream comprising butene with the metathesis catalyst.

According to another embodiment, a metathesis catalyst for producing propylene is provided. The metathesis catalyst comprises an amorphous mesoporous silica foam with impregnated metal oxides. The metathesis catalyst has a pore size distribution of at least 3 nm to about 40 nm and a total pore volume of at least 0.700 cm$^3$/g. Total pore volume refers to total pore volume per unit weight.

Additional features and advantages of the present embodiments will be set forth in the detailed description which follows, and in part will be readily apparent to those skilled in the art from that description or recognized by practicing the described embodiments, including the detailed description which follows, the claims, as well as the appended drawings.

DETAILED DESCRIPTION

Figure 1:
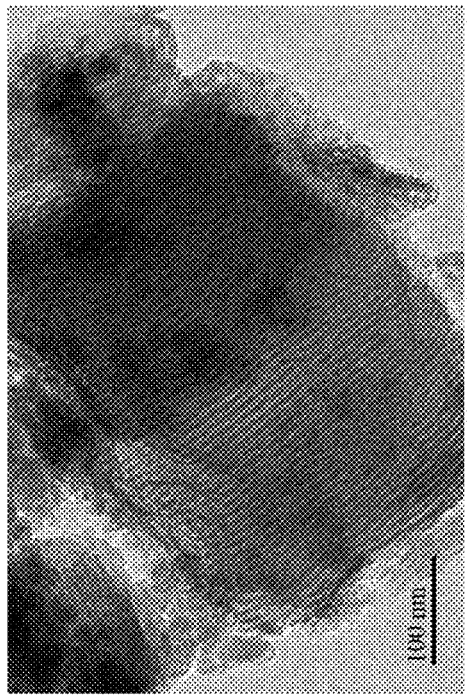
FIG. 1 is a Transmission Electron Microscopy (TEM) image of an amorphous mesoporous silica foam impregnated with 10% by weight tungsten oxide (WO$_3$) in accordance with one or more embodiments of the present disclosure.

Embodiments of the present disclosure are directed to systems and methods for converting a butene stream to propylene via catalyzed metathesis. As used in the application, "metathesis" is generally a two-step process: 2-butene isomerization and then cross-metathesis using the metathesis catalyst as depicted as follows in Formulas 1 and 2.

Formula 1: 2-Butene Isomerization

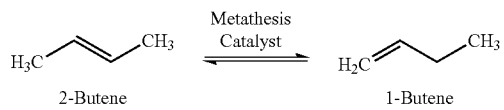

Formula 2: Cross-Metathesis

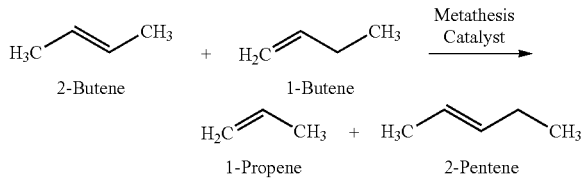

As shown in Formulas 1 and 2, the "metathesis" reactions are not limited to these reactants and products; however, this is the basic illustration of the reaction methodology. As shown, metathesis reactions take place between two alkene molecules. The groups bonded to the carbon atoms of the double bond are exchanged between the molecules to produce two new alkenes with the swapped groups. The specific catalyst that is selected for the olefin metathesis reaction helps to determine whether a cis-isomer or trans-isomer is formed, as the coordination of the olefin molecules with the catalyst play an important role, as do the steric influences of the substituents on the double bond of the newly formed molecule.

Here, the metathesis catalyst may comprise amorphous mesoporous silica foam impregnated with metal oxides. As used in the application, "amorphous mesoporous silica foam" means a silica support with a non-ordered structure and a narrow pore size distribution. This non-ordered structure may be random and thus different than the disclosed hexagonal or cubic structures of conventional silica supports. Specifically, the amorphous mesoporous silica foam has a narrow pore size distribution of at least 3 nm to about 40 nm and a total pore volume of at least 0.700 cm$^3$/g. Without being bound by theory, the present pore size distribution and pore volume are sized to achieve better catalytic activity and reduced blocking of pores by metal oxides, whereas smaller pore volume and pore size metathesis catalysts are susceptible to pore blocking and thereby reduced catalytic activity. Reduced blocking leads to higher dispersion of metal oxide species, such as $WO_3$, on the amorphous mesoporous silica foam. Higher $WO_3$ dispersion leads to higher metathesis activity and thus higher propylene yield.

In one or more embodiments, the pore size distribution may range from at least 3 nm to about 40 nm, or from about 3 nm to about 20 nm, or from about 4 nm to about 10 nm, or from about 4 nm to about 8 nm, or from about 4 nm to about 6 nm. In further embodiments, the total pore volume may be from at least 0.700 cm$^3$/g to about 2.5 cm$^3$/g, or from about 0.800 cm$^3$/g to about 2.5 cm$^3$/g, or from about 0.800 cm$^3$/g to about 1.5 cm$^3$/g, or from about 0.800 cm$^3$/g to about 1.25 cm$^3$/g, or from about 0.800 cm$^3$/g to about 1.0 cm$^3$/g, or from about 0.850 cm$^3$/g to about 1.0 cm$^3$/g.

Moreover, the metathesis catalyst has a total acidity from about 0.125 millimole/gram (mmol/g) to about 0.500 mmol/g. Without being bound by theory, if the material exceeds 0.500 mmol/g, other detrimental side reactions may result, such as cracking and hydrogen transfer reactions. In further embodiments, the metathesis catalyst may have a total acidity from about 0.125 mmol/g to about 0.250 mmol/g, or from about 0.125 mmol/g to about 0.150 mmol/g. While various surface areas are contemplated, the metathesis catalyst may, in one or more embodiments, have a surface area of at least about 400 meters$^2$/g, (m$^2$/g) or from about 400 m$^2$/g about 800 m$^2$/g, or from about 400 m$^2$/g to about 500 m$^2$/g, or from about 400 m$^2$/g to about 450 m$^2$/g, or from about 425 m$^2$/g to about 450 m$^2$/g.

The catalyst of the metathesis reaction is the impregnated metal oxide of the silica foam. The metal oxide may comprise one or oxides of a metal from the Periodic Table IUPAC Group Numbers 6-10. In one or more embodiments, the metal oxide may be an oxide of molybdenum, rhenium, tungsten, or combinations thereof. In a specific embodiment, the metal oxide is tungsten oxide ($WO_3$). It is contemplated that various amounts of metal oxide may be impregnated into the amorphous mesoporous silica foam. For example and not by way of limitation, the molar ratio of silica to metal oxide, for example, $WO_3$, is about 1 to about 50, or about 1 to about 40, or about 5 to about 30, or about 5 to about 15. Moreover, the metathesis catalyst may include from about 1 to about 50% by weight, or from about 2 to about 25% by weight, or from about 5 to about 15% by weight metal oxide, for example, $WO_3$.

Additionally, other optional components may be included into the impregnated mesoporous silica foam catalyst. For example, the metathesis catalyst may include a structuring agent. In one embodiment, the structuring agent is a tri-block copolymer structuring agent. In a further embodiment, the tri-block copolymer structuring agent is a poly(ethylene glycol)-block-poly(propylene glycol)-block-poly(ethylene glycol) structure, which may be also called a poloxamer structure. One suitable commercial embodiment of the surfactant tri-block copolymer structuring agent is Pluronic® P123 by BASF Corporation.

In operation, a product stream comprising propylene is produced from a stream comprising butene via metathesis conversion by contacting the metathesis catalyst. The butene stream comprises 2-butene, and optionally comprises one or more isomers, such as 1-butene, trans-2-butene, and cis-2-butene. The present discussion centers on butene based feed streams; however, it is known that other $C_1$-$C_6$ components may also be present in the feed stream. As shown previously, metathesis involves isomerization of 2-butene to 1-butene followed by cross-metathesis of the 2-butene and 1-butene into a metathesis product stream comprising propylene, and other alkenes/alkanes such as pentene.

Various systems which incorporate the metathesis catalyst are contemplated. For details regarding such systems, co-pending Saudi Aramco U.S. Application No. 62/188,052 entitled Systems and Methods of Producing Propylene is incorporated by reference in its entirety.

Various operating conditions are contemplated for the contacting of the butene stream with the catalyst. For example, the butene stream may contact the metathesis catalyst at a space hour velocity of about 10 to about 10,000 hr$^{-1}$, or about 300 to about 1200 hr$^{-1}$. Moreover, the butene stream may contact the metathesis catalyst at a temperature of about 200 to about 600° C., or about 300 to about 600° C. Furthermore, the butene stream may contact the metathesis catalyst at a pressure of about 1 to about 30 bars, or about 1 to about 10 bars. Optionally, the metathesis catalyst may be pretreated prior to metathesis. For example, the metathesis catalyst may be pretreated with $N_2$ for about 1 to about 5 hours before metathesis at a temperature of at least about 400° C., or at least about 500° C.

In one or more embodiments, the product stream may comprise at least about 35 mol. % propylene, and less than 1 mol. % aromatics. Without being bound by theory, it is desired that the aromatics yield be low as it causes coke formation, which can lead to catalyst deactivation. Without being bound by theory, the improved propylene yield and reduced side reactions is due in part to the high selectivity of the isomerization from 2-butene to 1-butene. For example, the present metathesis catalysts may yield at least 90% by weight, or at least 95% by weight conversion of 2-butene to 1-butene via isomerization. Moreover, by increasing the yield of 1-butene via isomerization, the subsequent cross-metathesis of 2-butene and 1-butene is able to yield more propylene in the product stream.

As will be demonstrated in the examples which follow, tungsten loaded on the amorphous mesoporous silica foam has higher 2-butene conversion and better propylene yield compared to tungsten loaded on ordered silica supports such as MCM-41 and SBA-15. Reiterating the prior statements, the selective isomerization of 2-butene to 1-butene and less hydrogen transfer reactions (less aromatics formation) are additional advantages of amorphous mesoporous silica foam as compared to MCM-41 and SBA-15. The formation of undesirable isobutylene is also reduced in amorphous mesoporous silica foam as compared to MCM-41 and SBA-15.

While various other metathesis catalysts are contemplated, the following method for producing a tungsten oxide impregnated mesoporous silica catalyst comprises preparing a precursor silica foam solution by mixing an aqueous triblock co-polymer surfactant solution with a sodium silicate solution, solidifying the precursor silica foam solution via a drying step, calcining the solid precursor silica foam, wet impregnating tungsten oxide into the solid precursor silica foam after calcining, and drying after wet impregnation to produce the tungsten oxide impregnated mesoporous silica catalyst. The aqueous triblock co-polymer surfactant solution includes an acid and a salt. The acid may comprise acetic acid and the salt may comprise ammonium fluoride

EXAMPLES

Example 1

Preparation of $WO_3$/Silica Foam (Catalyst-A)

The mesoporous silica foam with ultra large pores was synthesized using the following method. In a typical synthesis, 3.0 grams (g) of neutral triblock co-polymer surfactant, Pluronic® P123, was dissolved in a mixture of acetic acid (3.0 g), deionized (DI) water (52 g), and ammonium fluoride (0.3 g) at 40° C. After stirring for 2 hours, a solution of sodium silicate (2.35 g) in water (40 g) was added and the resultant mixture was reacted under vigorous stirring for 5 min. Then, the mixture was kept under static condition for 24 hours at 40° C. followed by aging at 70° C. overnight. The solid products were washed with DI water and collected by filtration and air dried. The obtained solid was then calcined at 560° C. for 6 hours to remove the template.

The silica foam was impregnated with 10% by weight of $WO_3$ following wet impregnation method. In a typical synthesis, 2 g of silica foam was suspended in 60 milliliters (ml) distilled water and 0.2112 g of ammonium metatungstate was added. The resulting mixture was stirred for 3 hours and dried overnight in the oven at 100° C. The material was calcined at 550° C. for 5 hours.

Example 2

Preparation of $WO_3$/SBA-15 (Catalyst B)

SBA-15 material was synthesized using tri-block copolymer, poly(ethylene glycol)-block-poly(propylene glycol)-block-poly(ethylene glycol) as a structure directing agent. In a typical synthesis, 4 g of Pluronic P123 was added to 30 ml of water. After stirring for a few hours, a clear solution was obtained. About 70 g of 0.28 Molar (M) hydrochloric acid was added to it and the solution was stirred for another 2 hours. Then, 9 g of tetraethyl orthosilicate (TEOS) was added and the resulting mixture was stirred for 24 hours at 40° C. and finally heated to 100° C. for 48 hours. The solid product was recovered by filtration, washed with water for several times, and dried overnight at 100° C. Finally, the product was calcined at 550° C. for 6 hours to remove the template.

The SBA-15 was impregnated with 10% by weight of $WO_3$ following a wet impregnation method. In a typical synthesis, 2 grams of silica foam was suspended in 60 ml distilled water and 0.2112 g of ammonium metatungstate was added. The resulting mixture was stirred for 3 hours and dried overnight in the oven at 100° C. The material was calcined at 550° C. for 5 hours.

Example 3

Preparation of $WO_3$/MCM-41(Catalyst-C)

The MCM-41 was synthesized following the procedure of Beck et al. [J. S. Beck, J. C. Vartuli, W. J. Roth, M. E. Leonowicz, C. T. Kresge, K. D. Schmitt, C. T.-U. Chu, D. H. Olsen, E. W. Sheppard, S. B. McCullen, J. B. Higgins, J. L. Schlenker, J. Am. Chem. Soc. 114, 10834 (1992)].

The MCM-41 was impregnated with 10% by weight of $WO_3$ following wet impregnation method. In a typical synthesis, 2 grams of silica foam was suspended in 60 ml distilled water and 0.2112 g of ammonium metatungstate was added. The resulting mixture was stirred for 3 hours and dried overnight in the oven at 100° C. The material was calcined at 550° C. for 5 hours.

Example 4

Catalyst Evaluation

The prepared catalysts were tested for their activity and selectivity to butene metathesis reaction in a fixed bed continuous flow reactor (ID 0.25 in, Autoclave Engineers Ltd) at atmospheric pressure. A fixed amount of catalyst sample (2 ml) was packed in the reactor tube with silicon carbide on top and bottom of the reactor. The catalyst was pretreated under $N_2$ at 550° C. for 1 hour. All reactions were carried out at 550° C., GHSV (gas hourly space velocity) of 900 $h^{-1}$ at atmospheric pressure using 2-butene (5 ml/min) as feed with nitrogen as diluent (25 ml/min). The quantitative analysis of the reaction products were carried out on-line using a Varian gas chromatograph with flame ionization detector (FID) (Varian 450-GC), equipped with CP—$Al_2O_3$/$Na_2SO_4$ capillary column (50 meters (m) length×0.32 millimeters (mm) I.D.×film thickness (df)=5 micrometers (μm)).

The physico-chemical parameters observed for catalyst A-C are presented in Table 1. Catalyst A has higher pore size and pore volume compared to catalyst B and C. This shows that the impregnation of $WO_3$ does not block the pores of catalyst A. The total acidity of catalyst A is also higher than catalyst B and C, indicating higher dispersion of tungsten oxides in the support.

TABLE 1

| Catalysts | Surface Area (m²/g) | Pore Size Distribution (nm) | Total Pore Volume (cm³/g) | Total Acidity (mmol./g) |
|---|---|---|---|---|
| 10% WO₃/Silica Foam (A) | 436 | 4.07 | 0.887 | 0.129 |
| 10% WO₃/MCM-41 (B) | 419 | 2.1 | 0.453 | 0.118 |
| 10% WO₃/SBA-15 (C) | 468 | 2.73 | 0.636 | 0.108 |

Figure 2:
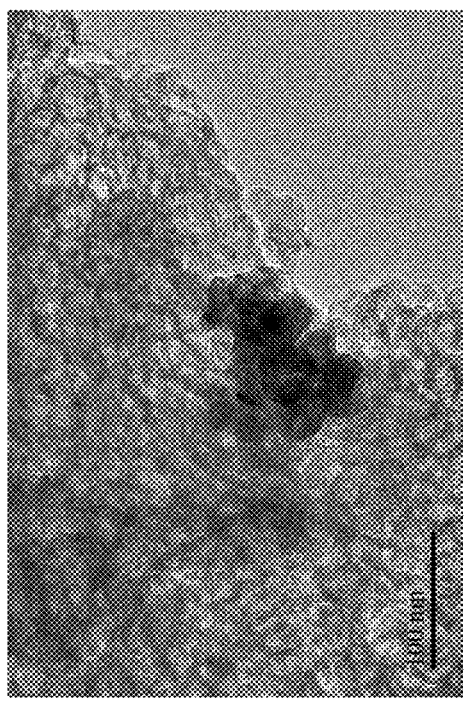
FIG. 2 is a TEM image of an SBA-15 silica support impregnated with WO$_3$.
Figure 3:
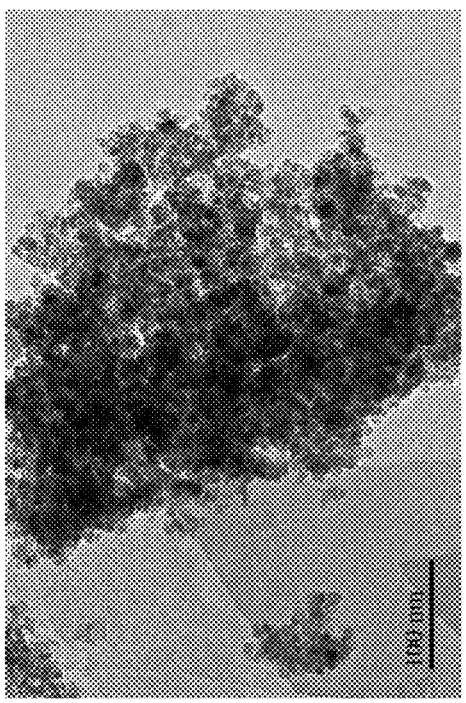
FIG. 3 is a TEM image of an MCM-41 support impregnated with WO$_3$.

Transmission electron microscopy (TEM) images of the catalysts were performed on a JEOL JEM 3010 electron microscope operated at 200 kilovolts (kV). The catalysts were dispersed in methanol by sonication. Few drops of the dispersion were dropped onto a carbon-coated copper grid followed by solvent evaporation in air at room temperature. FIGS. 1-3 present TEM images of the three samples. FIG. 1 illustrates that 10 W/Silica Foam exhibits that tungsten is well dispersed as compared with 10 W/SBA-15 as depicted in FIGS. 2 and 10 W/MCM-41 as depicted in FIG. 3. The agglomeration of tungsten species was lower for 10 W/Silica Foam than 10 W/SBA-15 and 10 W/MCM-41. This shows that the 10W/Silica Foam has more active species available for metathesis reaction compared to other catalysts.

Example 5

Isomerization Performance

Figure 4:
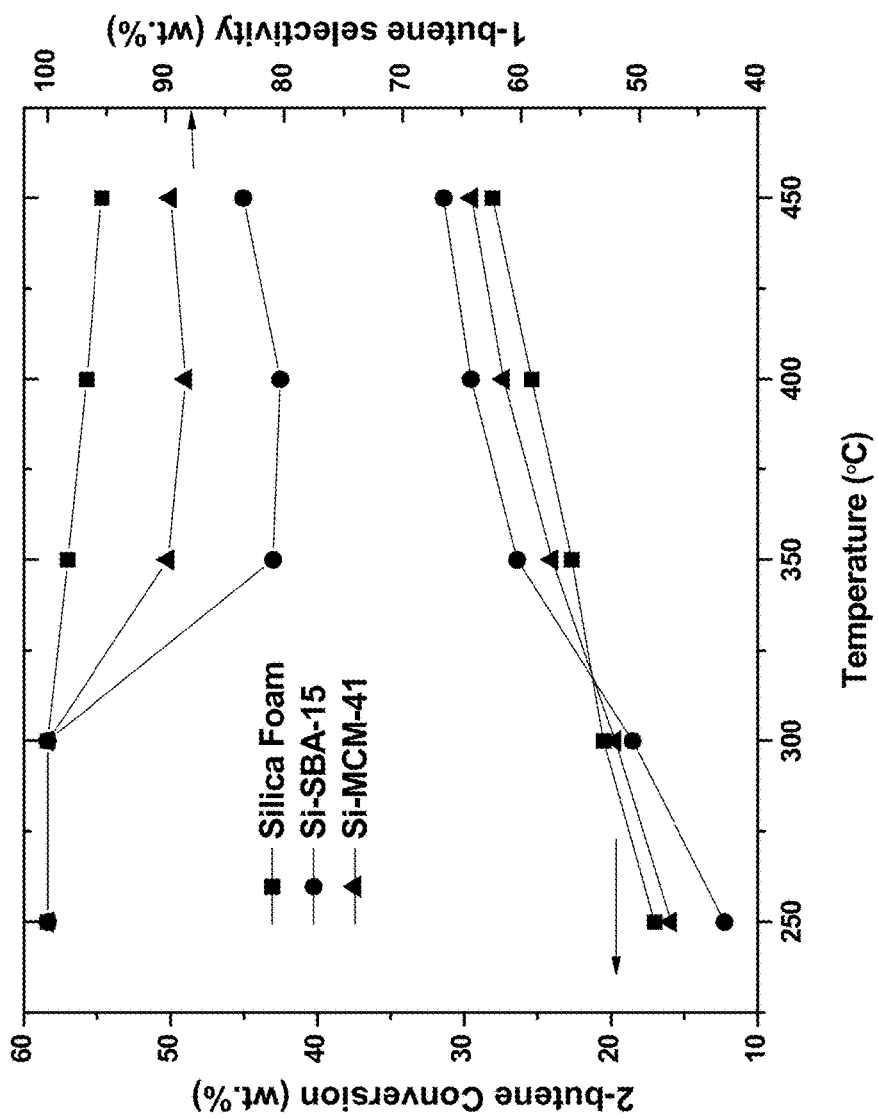
FIG. 4 is a graph illustrating the isomerization activity and 2-butene conversion of the catalysts from FIGS. 1-3 in accordance with one or more embodiments of the present disclosure.

The graph of FIG. 4 illustrates the isomerization activity and 2-butene conversion of the catalyst from FIGS. 1-3 at a GHSV (gas hourly space velocity) of 900 h⁻¹ at atmospheric pressure using 2-butene (5 ml/min) as feed with nitrogen as diluent (25 ml/min). As shown, while the 2-butene conversion (depicted on left side Y-axis) yielded similar results for the catalysts A-C; however, 2-butene isomerization to 1-butene greatly differs among catalyst A-C. Specifically, the silica foam catalyst A has a selectivity value of 95% by weight at 450 C, whereas the other catalysts B and C are at 90% or less. As stated, a higher isomerization selectivity increases the amount of propylene yielded in the cross-metathesis step. Also, a higher isomerization selectivity also reduces side reactions which can cause coking and catalyst deactivation.

Example 6

Metathesis Performance

Table 2 shows the metathesis activity of catalysts A-C at 550° C. (GHSV 900 h⁻¹). Catalytic performances of catalysts A-C in the metathesis reaction of 2-butene (Reaction temperature: 550° C., atmospheric pressure, GHSV 900 h⁻¹). Catalyst A prepared with silica foam as support shows higher 2-butene conversion and better propylene yield as compared to catalysts B and C. Higher yield of catalyst A relates to selective isomerization of 2-butene to 1-butene, which undergo further cross-metathesis reaction to produce propylene. Catalyst A has a large pore diameter, which provides higher dispersion of WO₃ species leading to high metathesis activity. The acidity of the material plays an important role in the isomerization of 2-butene to 1-butene, which enhances the activity of metathesis reaction between 2-butene and 1-butene. The yield of aromatics and higher compounds were found to be less for catalyst A compared to other catalysts thereby showing higher metathesis activity of the catalyst A.

TABLE 2

| Yield (Mol. %) | 10 W/Silica Foam (A) | 10 W/SBA-15 (B) | 10 W/MCM-41 (C) |
|---|---|---|---|
| $C_2$= | 10.67 | 8.35 | 8.79 |
| $C_3$= | 35.95 | 33.29 | 31.84 |
| 1-$C_4$= | 8.41 | 10.57 | 9.38 |
| 2-$C_4$= | 17.47 | 23.28 | 19.78 |
| i-$C_4$= | 5.78 | 2.02 | 8.48 |
| $C_5$= | 20.79 | 21.33 | 19.19 |
| $C_6$+ | 0.93 | 1.16 | 2.54 |

Calculation Methodologies

The surface area of the samples was measured by nitrogen adsorption at 77 K using AUTOSORB-1 (Quanta Chrome). Before adsorption measurements, samples (ca. 0.1 g) were heated at 220° C. for 2 h under nitrogen flow. The nitrogen adsorption isotherms of catalysts were measured at liquid nitrogen temperature (77 K). The surface areas and pore size distributions were calculated by the Brunauer Emmett-Teller (BET) method and the Barrett-Joyner-Halenda (BJH) method, respectively. The total pore volume was estimated from the amount of $N_2$ adsorbed at P/P0=0.99. Barret E P, Joyner L J, Halenda P H, J. Am. Chem. Soc. 73 (1951) 373-380.

The zeolite samples were characterized by X-ray powder diffraction (XRD) with a Rigaku Mini-flex II system using nickel filtered CuKα radiation (λ=1.5406 Å, 30 kV and 15 mA). The XRD patterns were recorded in static scanning mode from 1.2-50° (2θ) at a detector angular speed of 2° min⁻¹ with a step size of 0.02°.

It should now be understood that various aspects of the methods of making propylene with the metathesis catalysts are described in the application and that such aspects may be utilized in conjunction with various other aspects.

In a first aspect, the disclosure provides a metathesis process for producing propylene comprising providing a metathesis catalyst comprising an amorphous mesoporous silica foam impregnated with metal oxides, where the metathesis catalyst has a pore size distribution of at least 3 nm to about 40 nm and a total pore volume of at least 0.700 cm³/g, The process further comprises producing a product stream comprising propylene by contacting a feed stream comprising butene with the metathesis catalyst.

In a second aspect, the disclosure provides a process of the first aspect, in which the process further comprises tri-block copolymer structuring agent, where the tri-block copolymer structuring agent is poly(ethylene glycol)-block-poly(propylene glycol)-block-poly(ethylene glycol) structure.

In a third aspect, the disclosure provides a process of either the first or second aspects, in which the metal oxides are impregnated via wet impregnation.

In a fourth aspect, the disclosure provides a process of any one of the first through third aspects, in which the feed stream comprises 2-butene, and optionally one or more of 1-butene, trans-2-butene, and cis-2-butene.

In a fifth aspect, the disclosure provides a process of any one of the first through fourth aspects, in which the metathesis catalyst catalyzes isomerization of 2-butene to 1-butene followed by cross-metathesis of 2-butene and 1-butene into a metathesis product stream comprising propylene, where at least 90% of the 2-butene is converted to 1-butene via isomerization.

In a sixth aspect, the disclosure provides a process of any one of the first through fifth aspects, in which the pore size distribution is from at least 4 nm to about 10 nm.

In a seventh aspect, the disclosure provides a process of any one of the first through sixth aspects, in which the total pore volume is from at least 0.800 cm$^3$/g to about 1.5 cm$^3$/g.

In an eighth aspect, the disclosure provides a process of any one of the first through seventh aspects, in which the metathesis catalyst has a total acidity from about 0.125 mmol/g to about 0.500 mmol/g.

In a ninth aspect, the disclosure provides a process of any one of the first through eighth aspects, in which the metal oxide comprises one or oxides of a metal from the Periodic Table IUPAC group numbers 6-10.

In a tenth aspect, the disclosure provides a process of any one of the first through ninth aspects, in which the metal oxide is an oxide of molybdenum, rhenium, tungsten, or combinations thereof.

In an eleventh aspect, the disclosure provides a process of any one of the first through tenth aspects, in which the metal oxide is tungsten oxide.

In a twelfth aspect, the disclosure provides a process of any one of the first through eleventh aspects, in which the metathesis catalyst comprises from about 5 to about 15% by weight metal oxide.

In a thirteenth aspect, the disclosure provides a process of any one of the first through twelfth aspects, in which the metathesis catalyst has a surface area of about 400 to about 500 m$^2$/g.

In a fourteenth aspect, the disclosure provides a process of any one of the first through thirteenth aspects, further comprising pre-treating the metathesis catalyst with N$_2$ about 1 to about 5 hours before metathesis at a temperature of at least about 500° C.

In a fifteenth aspect, the disclosure provides a process of any one of the first through fourteenth aspects, in which the contact between the butene and the metathesis catalyst occurs at a space hour velocity of about 10 to about 10,000 hr$^{-1}$, a temperature of about 300 to about 600° C., and a pressure of about 1 to about 10 bars.

In a sixteenth aspect, the disclosure provides a process of any one of the first through fifteenth aspects, in which the product stream comprises at least about 35 mol. % propylene.

In a seventeenth aspect, the disclosure provides a process of any one of the first through sixteenth aspects, in which the product stream comprises at least about 10 mol. % ethylene.

In an eighteenth aspect, the disclosure provides a process of any one of the first through seventeenth aspects, in which the product stream comprises less than 1 mol. % aromatics.

In a nineteenth aspect, the disclosure provides a metathesis catalyst for producing propylene suitable for use in any of the processes of the first through eighteenth aspects, where metathesis catalyst comprises an amorphous mesoporous silica foam with impregnated metal oxides, where the metathesis catalyst has a pore size distribution of at least 3 nm to about 40 nm and a total pore volume of at least 0.700 cm$^3$/g.

In a twentieth aspect, the disclosure provides a metathesis catalyst of the nineteenth aspect, further comprising a tri-block copolymer structuring agent, where the tri-block copolymer structuring agent is poly(ethylene glycol)-block-poly(propylene glycol)-block-poly(ethylene glycol) structure.

In a twenty-first aspect, the disclosure provides a metathesis catalyst of the nineteenth or twentieth aspects, in which the pore size distribution is from at least 4 nm to about 10 nm.

In a twenty-second aspect, the disclosure provides a metathesis catalyst of any one of the nineteenth through twenty-first aspects, in which the total pore volume is from at least 0.800 cm$^3$/g to about 1.5 cm$^3$/g.

In a twenty-third aspect, the disclosure provides a metathesis catalyst of any one of the nineteenth through twenty-second aspects, in which the metathesis catalyst has a total acidity from about 0.125 mmol/g to about 0.500 mmol/g.

In a twenty-fourth aspect, the disclosure provides a metathesis catalyst of any one of the nineteenth through twenty-third aspects, in which where the metal oxide is an oxide of molybdenum, rhenium, tungsten, or combinations thereof.

In a twenty-fifth aspect, the disclosure provides a metathesis catalyst of any one of the nineteenth through twenty-fourth aspects, in which the metal oxide is tungsten oxide.

In a twenty-sixth aspect, the disclosure provides a metathesis catalyst of any one of the nineteenth through twenty-fifth aspects, in which the amorphous mesoporous silica foam has a molar ratio for silica to tungsten oxide of about 1 to about 50.

In a twenty-seventh aspect, the disclosure provides a metathesis catalyst of any one of the nineteenth through twenty-sixth aspects, in which the metathesis catalyst comprises from about 5 to about 15% by weight metal oxide.

In a twenty-eighth aspect, the disclosure provides a metathesis catalyst of any one of the nineteenth through twenty-seventh aspects, in which the metathesis catalyst has a pore size ranging from about 2 nm to about 4 nm.

In a twenty-ninth aspect, the disclosure provides a metathesis catalyst of any one of the nineteenth through twenty-eighth aspects, in which metathesis catalyst has a surface area of about 400 to about 500 m$^2$/g.

It should be apparent to those skilled in the art that various modifications and variations can be made to the described embodiments without departing from the spirit and scope of the claimed subject matter. Thus it is intended that the specification cover the modifications and variations of the various described embodiments provided that such modification and variations come within the scope of the appended claims and their equivalents.

What is claimed is:

1. A metathesis process for producing propylene comprising:
   providing a metathesis catalyst comprising an amorphous mesoporous silica foam impregnated with metal oxides, where the metathesis catalyst has a pore size distribution of at least 3 nm to 40 nm and a total pore volume of at least 0.700 cm$^3$/g; and
   producing a product stream comprising propylene by contacting a feed stream comprising butene with the metathesis catalyst, where the metathesis catalyst has a total acidity from 0.125mmol/g to 0.500 mmol/g, and a surface area of 400 to 500 m$^2$/g.

2. The process of claim 1 further comprising tri-block copolymer structuring agent, where the tri-block copolymer structuring agent is poly(ethylene glycol)-block-poly(propylene glycol)-block-poly(ethylene glycol) structure.

3. The process of claim 2 where the metathesis catalyst catalyzes isomerization of 2-butene to 1-butene followed by cross-metathesis of 2-butene and 1-butene into a metathesis product stream comprising propylene.

4. The process of claim 3 where at least 90% of the 2-butene is converted to 1-butene via isomerization.

5. The process of claim 1 where the pore size distribution is from at least 4 nm to 10 nm and the total pore volume is from at least 0.800 cm$^3$/g to 1.5 cm$^3$/g.

6. The process of claim 1 where the metal oxide is an oxide of molybdenum, rhenium, tungsten, or combinations thereof.

7. The process of claim 1 where the metal oxide is tungsten oxide.

8. The process of claim 7 where the metathesis catalyst has a molar ratio for silica to tungsten oxide of 1 to 50.

9. The process of claim 7 where the metathesis catalyst comprises from 5 to 15% by weight tungsten oxide.

10. A metathesis catalyst for producing propylene comprising
    an amorphous mesoporous silica foam with impregnated metal oxides, where the metathesis catalyst has a pore size distribution of at least 3 nm, to 40 nm, a total pore volume of at least 0.700 cm$^3$/g, a total acidity from 0.125 mmol/g to 0.500 mmol/g, and a surface area of 400 to 500 m$^2$/g.

11. The metathesis catalyst of claim 10 further comprising a tri-block copolymer structuring agent, where the tri-block copolymer structuring agent is poly(ethylene glycol)-block-poly(propylene glycol)-block-poly(ethylene glycol) structure.

12. The metathesis catalyst of claim 10 where the pore size distribution is from at least 4 nm to 10 nm, and the total pore volume is from at least 0.800 cm$^3$/g to 1.5 cm$^3$/g.

13. The metathesis catalyst of claim 10 where the metal oxide is an oxide of molybdenum, rhenium, tungsten, or combinations thereof.

14. The metathesis catalyst of claim 10 where the metal oxide is tungsten oxide.

15. The metathesis catalyst of claim 14 where the metathesis catalyst has a molar ratio for silica to tungsten oxide of 1 to 50.

16. The metathesis catalyst of claim 10 where the metathesis catalyst comprises from 5 to 15% by weight metal oxide.

17. The metathesis catalyst of claim 10 where the metathesis catalyst has a pore size ranging from 2 nm to 4 nm.

* * * * *